US010226333B2

(12) United States Patent
Al-Jilaihawi et al.

(10) Patent No.: US 10,226,333 B2
(45) Date of Patent: Mar. 12, 2019

(54) ANATOMICALLY-ORIENTATED AND SELF-POSITIONING TRANSCATHETER MITRAL VALVE

(71) Applicant: Cedars-Sinai Medical Center, Los Angeles, CA (US)

(72) Inventors: Hasanian Al-Jilaihawi, West Hollywood, CA (US); Rajendra Makkar, Los Angeles, CA (US)

(73) Assignee: Cedars-Sinai Medical Center, Los Angeles, CA (US)

(*) Notice: Subject to any disclaimer, the term of this patent is extended or adjusted under 35 U.S.C. 154(b) by 211 days.

(21) Appl. No.: 15/022,900

(22) PCT Filed: Oct. 14, 2014

(86) PCT No.: PCT/US2014/060526
§ 371 (c)(1),
(2) Date: Mar. 17, 2016

(87) PCT Pub. No.: WO2015/057735
PCT Pub. Date: Apr. 23, 2015

(65) Prior Publication Data
US 2016/0206424 A1    Jul. 21, 2016

Related U.S. Application Data

(60) Provisional application No. 61/891,003, filed on Oct. 15, 2013.

(51) Int. Cl.
*A61F 2/24*    (2006.01)
(52) U.S. Cl.
CPC .......... *A61F 2/2412* (2013.01); *A61F 2/2418* (2013.01); *A61F 2/2433* (2013.01);
(Continued)

(58) Field of Classification Search
CPC ............ A61F 2230/0034; A61F 2/2418; A61F 2/2436; A61F 2220/0016;
(Continued)

(56) References Cited

U.S. PATENT DOCUMENTS 4,694,838 A    9/1987 Wijayarthna et al.
4,738,667 A    4/1988 Galloway
(Continued)

FOREIGN PATENT DOCUMENTS

CN    105611871 A    5/2016
CN    105611889 A    5/2016
(Continued)

OTHER PUBLICATIONS

PCT/US2014/060957 International Preliminary Report on Patentability dated Apr. 19, 2016, 10 pages.
(Continued)

*Primary Examiner* — Eric J Rosen
*Assistant Examiner* — George J Ulsh
(74) *Attorney, Agent, or Firm* — Nixon Peabody LLP

(57) ABSTRACT

Described herein is a mitral valve and systems and methods for implanting the same. The mitral valve device is designed to easily orient to and conform to the mitral orifice natural morphology. This mitral valve system may be implanted using a system of 2 guide wires that facilitate orientation of the flat portion of the stent properly with the flat portion of the mitral valve that is adjacent to the aortic valve. Additionally, the disclosed valve may have multiple mounds distributed across the outer surface of the valve/stent complex so as to prevent or reduce paravalvular leak after implantation.

11 Claims, 11 Drawing Sheets

(52) U.S. Cl.
CPC .... *A61F 2/2436* (2013.01); *A61F 2220/0016* (2013.01); *A61F 2230/0034* (2013.01); *A61F 2250/0003* (2013.01); *A61F 2250/006* (2013.01); *A61F 2250/0063* (2013.01); *A61F 2250/0067* (2013.01)

(58) Field of Classification Search
CPC ........ A61F 2250/0003; A61F 2250/006; A61F 2250/0063; A61F 2250/0067; A61F 2/2412; A61F 2/2433
See application file for complete search history.

(56) References Cited

U.S. PATENT DOCUMENTS

| | | | |
|---|---|---|---|
| 5,423,829 | A | 6/1995 | Pham et al. |
| 5,964,744 | A | 10/1999 | Balbierz et al. |
| 5,964,797 | A | 10/1999 | Ho |
| 5,972,019 | A | 10/1999 | Engleson et al. |
| 6,059,779 | A | 5/2000 | Mills |
| 6,086,557 | A | 7/2000 | Morejohn et al. |
| 6,217,611 | B1 | 4/2001 | Klostermeyer |
| 6,287,277 | B1 | 9/2001 | Yan |
| 6,350,282 | B1 | 2/2002 | Eberhardt |
| 6,589,230 | B2 | 7/2003 | Gia et al. |
| 6,953,473 | B2 | 10/2005 | Porter |
| 6,964,657 | B2 | 11/2005 | Cragg et al. |
| 6,976,965 | B2 | 12/2005 | Corl et al. |
| 7,134,994 | B2 | 11/2006 | Alpert et al. |
| 7,340,288 | B1 | 3/2008 | Karicherla et al. |
| 7,935,144 | B2 | 5/2011 | Robin et al. |
| 8,070,800 | B2 | 12/2011 | Lock et al. |
| 8,092,524 | B2 | 1/2012 | Nugent et al. |
| 8,372,069 | B2 | 2/2013 | Kassab |
| 8,377,112 | B2 | 2/2013 | Griffin et al. |
| 8,408,214 | B2 | 4/2013 | Spenser |
| 8,430,927 | B2 | 4/2013 | Bonhoeffer |
| 8,491,648 | B2 | 7/2013 | Hassan et al. |
| 2002/0169474 | A1 | 11/2002 | Kusleika et al. |
| 2004/0172081 | A1 | 9/2004 | Wang |
| 2005/0203425 | A1 | 9/2005 | Langston |
| 2005/0240200 | A1 | 10/2005 | Bergheim |
| 2005/0256566 | A1 | 11/2005 | Gabbay |
| 2005/0267010 | A1 | 12/2005 | Goodson et al. |
| 2006/0064114 | A1 | 3/2006 | Obitsu et al. |
| 2006/0287719 | A1 | 12/2006 | Rowe et al. |
| 2007/0050021 | A1* | 3/2007 | Johnson ................ A61F 2/2418 623/2.14 |
| 2007/0203562 | A1 | 8/2007 | Malewicz et al. |
| 2008/0027334 | A1 | 1/2008 | Langston |
| 2008/0033467 | A1 | 2/2008 | Miyamoto et al. |
| 2008/0183273 | A1 | 7/2008 | Mesana et al. |
| 2008/0221551 | A1 | 9/2008 | Goodson et al. |
| 2008/0306499 | A1 | 12/2008 | Katoh et al. |
| 2008/0319541 | A1 | 12/2008 | Filsoufi |
| 2009/0082678 | A1 | 3/2009 | Smith |
| 2009/0248143 | A1 | 10/2009 | Laham |
| 2009/0259292 | A1 | 10/2009 | Bonhoeffer |
| 2009/0276040 | A1 | 11/2009 | Rowe et al. |
| 2010/0030330 | A1 | 2/2010 | Bobo et al. |
| 2010/0094209 | A1 | 4/2010 | Drasler et al. |
| 2010/0168840 | A1 | 7/2010 | Kassab |
| 2010/0185275 | A1 | 7/2010 | Richter et al. |
| 2010/0191272 | A1 | 7/2010 | Keating |
| 2010/0211094 | A1 | 8/2010 | Sargent |
| 2010/0331948 | A1 | 12/2010 | Turovskiy et al. |
| 2011/0137397 | A1 | 6/2011 | Chau et al. |
| 2012/0130230 | A1 | 5/2012 | Eichler et al. |
| 2012/0158129 | A1 | 6/2012 | Duffy et al. |
| 2012/0283757 | A1 | 11/2012 | Miller et al. |
| 2012/0283812 | A1 | 11/2012 | Lagodzki et al. |
| 2012/0283820 | A1 | 11/2012 | Tseng et al. |
| 2013/0090726 | A1 | 4/2013 | Rowe et al. |
| 2013/0109960 | A1 | 5/2013 | Stinis |
| 2013/0116779 | A1 | 5/2013 | Weber |
| 2013/0166017 | A1 | 6/2013 | Cartledge et al. |
| 2013/0190857 | A1 | 7/2013 | Mitra et al. |
| 2013/0190865 | A1 | 7/2013 | Anderson |
| 2013/0261738 | A1 | 10/2013 | Clague et al. |
| 2013/0261739 | A1 | 10/2013 | Kuehn |
| 2013/0274618 | A1 | 10/2013 | Hou et al. |
| 2013/0331921 | A1 | 12/2013 | Roubin |
| 2014/0114402 | A1 | 4/2014 | Ahlberg et al. |
| 2014/0135799 | A1 | 5/2014 | Henderson |
| 2014/0194981 | A1 | 7/2014 | Menk et al. |
| 2014/0200662 | A1 | 7/2014 | Eftel et al. |
| 2014/0222144 | A1 | 8/2014 | Eberhardt et al. |
| 2014/0236287 | A1 | 8/2014 | Clague et al. |
| 2014/0243966 | A1 | 8/2014 | Garde et al. |
| 2014/0277419 | A1 | 9/2014 | Garde et al. |
| 2014/0303719 | A1 | 10/2014 | Cox et al. |
| 2014/0350669 | A1 | 11/2014 | Gillespie et al. |
| 2016/0228013 | A1 | 8/2016 | Al-Jilaihawi et al. |
| 2016/0228241 | A1 | 8/2016 | Al-Jilaihawi et al. |
| 2016/0235422 | A1 | 8/2016 | Al-Jilaihawi et al. |
| 2016/0302920 | A1 | 10/2016 | Al-Jilaihawi |
| 2016/0310699 | A1 | 10/2016 | Al-Jilaihawi |

FOREIGN PATENT DOCUMENTS

| | | |
|---|---|---|
| CN | 105744969 A | 7/2016 |
| CN | 105764447 A | 7/2016 |
| EP | 3054838 A1 | 8/2016 |
| EP | 3057522 A1 | 8/2016 |
| EP | 3079633 A1 | 10/2016 |
| EP | 3099345 A1 | 12/2016 |
| WO | 1996017644 A1 | 6/1996 |
| WO | 99/15223 A1 | 4/1999 |
| WO | 99/15227 A1 | 4/1999 |
| WO | 1999015223 A1 | 4/1999 |
| WO | 0249511 A1 | 6/2002 |
| WO | 2005059379 A1 | 6/2005 |
| WO | 2007081820 A1 | 7/2007 |
| WO | 2010085659 A1 | 7/2010 |
| WO | 2011039091 A1 | 4/2011 |
| WO | 2012009675 A2 | 1/2012 |
| WO | 2012161769 A1 | 11/2012 |
| WO | 2012/173697 A1 | 12/2012 |
| WO | 2013061281 A1 | 5/2013 |
| WO | 2014145469 A1 | 9/2014 |
| WO | 2015/054296 A1 | 4/2015 |
| WO | 2015/057735 A1 | 4/2015 |
| WO | 2015/057995 A2 | 4/2015 |
| WO | 2015/058001 A1 | 4/2015 |
| WO | 2015/089334 A1 | 6/2015 |
| WO | 2015/117025 A1 | 8/2015 |
| WO | 2016145250 A1 | 9/2016 |

OTHER PUBLICATIONS

PCT/US2014/060966 International Preliminary Report on Patentability dated Apr. 19, 2016, 6 pages.
Extended European Search Report for EP Application No. 14853895.2 dated May 10, 2017, 8 pages.
Partial Supplementary European Search Report for EP Application No. 14851950.7 dated Apr. 10, 2017, 6 pages.
Extended European Search Report for EP Application No. 14869869.9 dated May 4, 2017, 7 pages.
PCT/US2016/021866 International Search Report and Written Opinion dated May 23, 2016, 11 pages.
Extended Search Report for EP 15743048.9 dated Aug. 24, 2017, 8 pages.
PCT/US2014/060526 International Preliminary Report on Patentability dated Apr. 28, 2016; 7 pages.
PCT/US2014/060526 International Search Report and Written Opinion dated Feb. 10, 2015; 7 pages.
PCT/US2014/060957 International Search Report and Written Opinion dated Apr. 1, 2015; 10 pages.
PCT/US2014/060966 International Search Report and Written Opinion dated Jan. 29, 2015; 6 pages.
PCT/US2014/059547 International Search Report and Written Opinion dated Mar. 3, 2015; 9 pages.

(56) References Cited

OTHER PUBLICATIONS

PCT/US2014/069849 International Search Report and Written Opinion dated Mar. 2, 2015; 8 pages.
PCT/US2015/013956 International Search Report and Written Opinion dated Jun. 26, 2015; 10 pages.
Astarci et al. Transapical explantation of an embolized transcatheter valve. Interact Cardiovasc Thorac Surg (2011). 13:1-2.
Blows et al. The pressure wire in practice. Heart (2007). 93:419-422.
Bonhoeffer et al. The multi-track angiography catheter: a new tool for complex catheterisation in congenital heart disease. Heart (1996). 76:173-177.
Chiam et al. Percutaneous Transcatheter Mitral Valve Repair. J Am Coll Cardiol (2011). 4(1):1-13.
Ho, S.Y. Structure and anatomy of the aortic root. Eur J Echocardiogr (2009). 10:i3-i10.
Jolicoeur et al. Tiara: A Novel Catheter-Based Mitral Valve Bioprosthesis Initial Experiments and Short-Term Pre-Clinical Results. J Am Coll Cardiol (2012). 60(15):1430-1431.
Lange et al. Diagnostic Cardiac Catheterization. Circulation (2003). 107:e111-e113.
Masson et al. Percutaneous Treatment of Mitral Regurgitation. Circ Cardiovasc Interv (2009). 2:140-146.
McCarthy et al. Anatomy of the mitral valve: understanding the mitral valve complex in mitral regurgitation. Eur J Echocardiogr (2010). 11:i3-i9.
Ormiston et al. Bioabsorbable Coronary Stents (2009). Circ Cardiovasc Interv (2009). 2:255-260.
Sievers et al. The everyday used nomenclature of the aortic root components: the tower of Babel? Eur J Cardio-Thorac Surg (2011). 0:1-5.
Sinning et al. Aortic Regurgitation Index Defines Severity of Peri-Prosthetic Regurgitation and Predicts Outcome in Patients After Transcatheter Aortic Valve Implantation. J Am Coll Cardiol (2012). 59(13):1134-1141.
Tonino et al. Fractional Flow Reserve versus Angiography for Guiding Percutaneous Coronary Intervention. New Engl J Med (2009). 360(3):213-224.
Tsai et al. Transcatheter Retrieval of Dislodged Port-A Catheter Fragments: Experience with 47 Cases. Acta Cardiol Sin (2006). 22:221-228.
Van Mieghem et al. Anatomy of the Mitral Valvular Complex and Its Implications for Transcatheter Interventions for Mitral Regurgitation. J Am Coll Cardiol (2010). 56(8):617-626.
PCT/US2014/069849 International Preliminary Report on Patentability dated Jun. 14, 2016; 7 pages.
PCT/US2015/013956 International Preliminary Report on Patentability dated Aug. 2, 2016; 7 pages.
PCT/US2014/059547 International Preliminary Report on Patentability dated Apr. 12, 2016; 6 pages.

\* cited by examiner

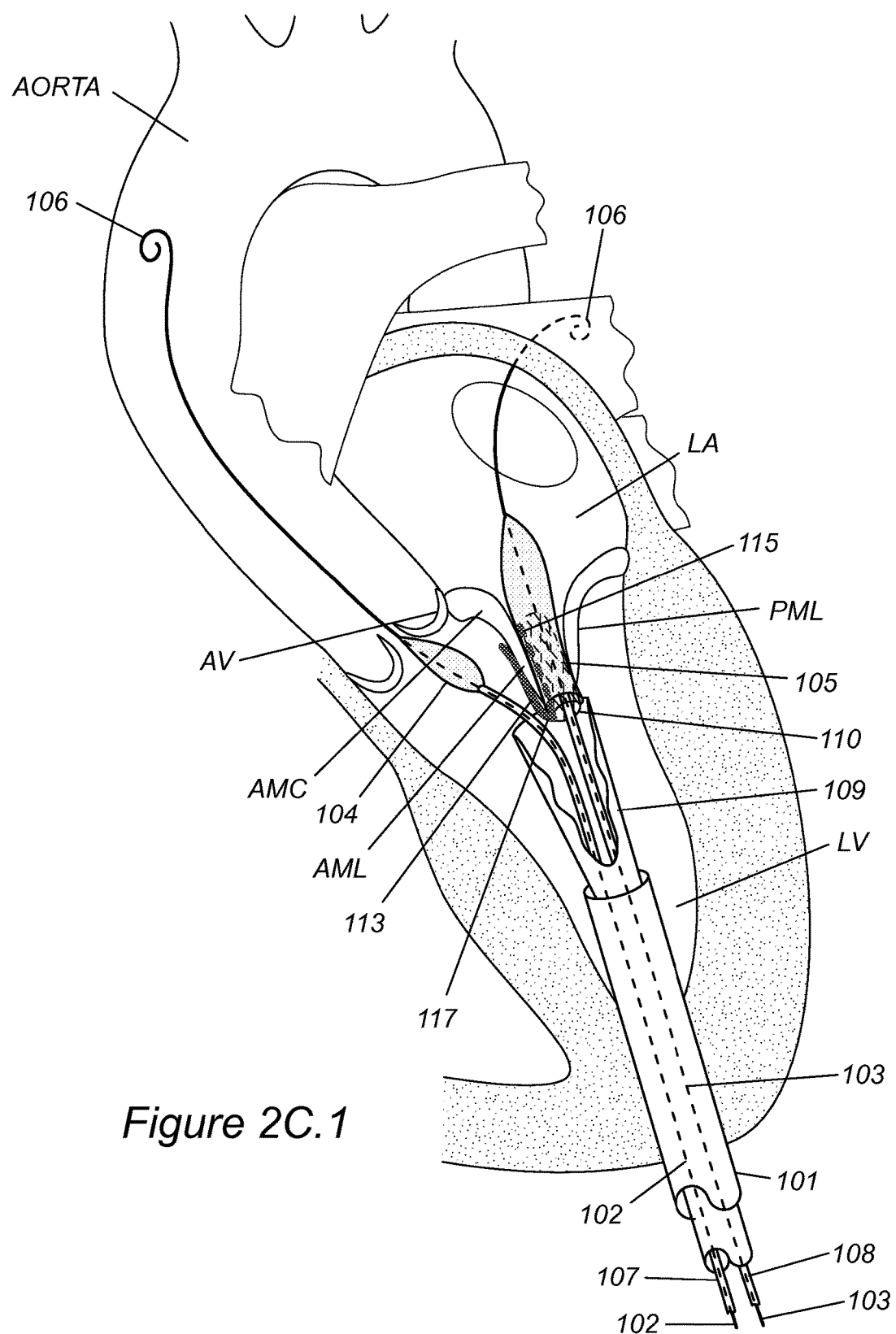
Figure 2C.1

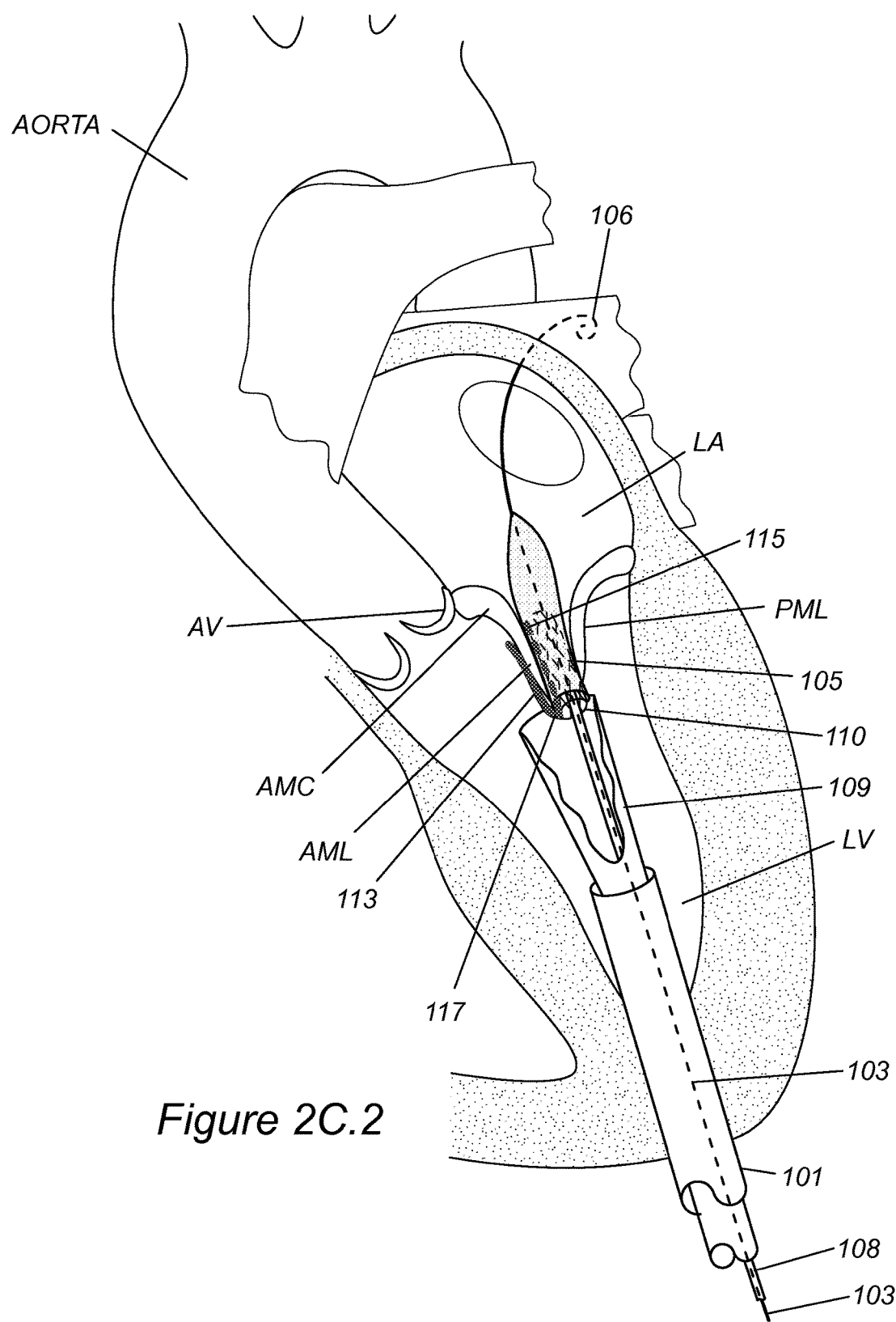
Figure 2C.2

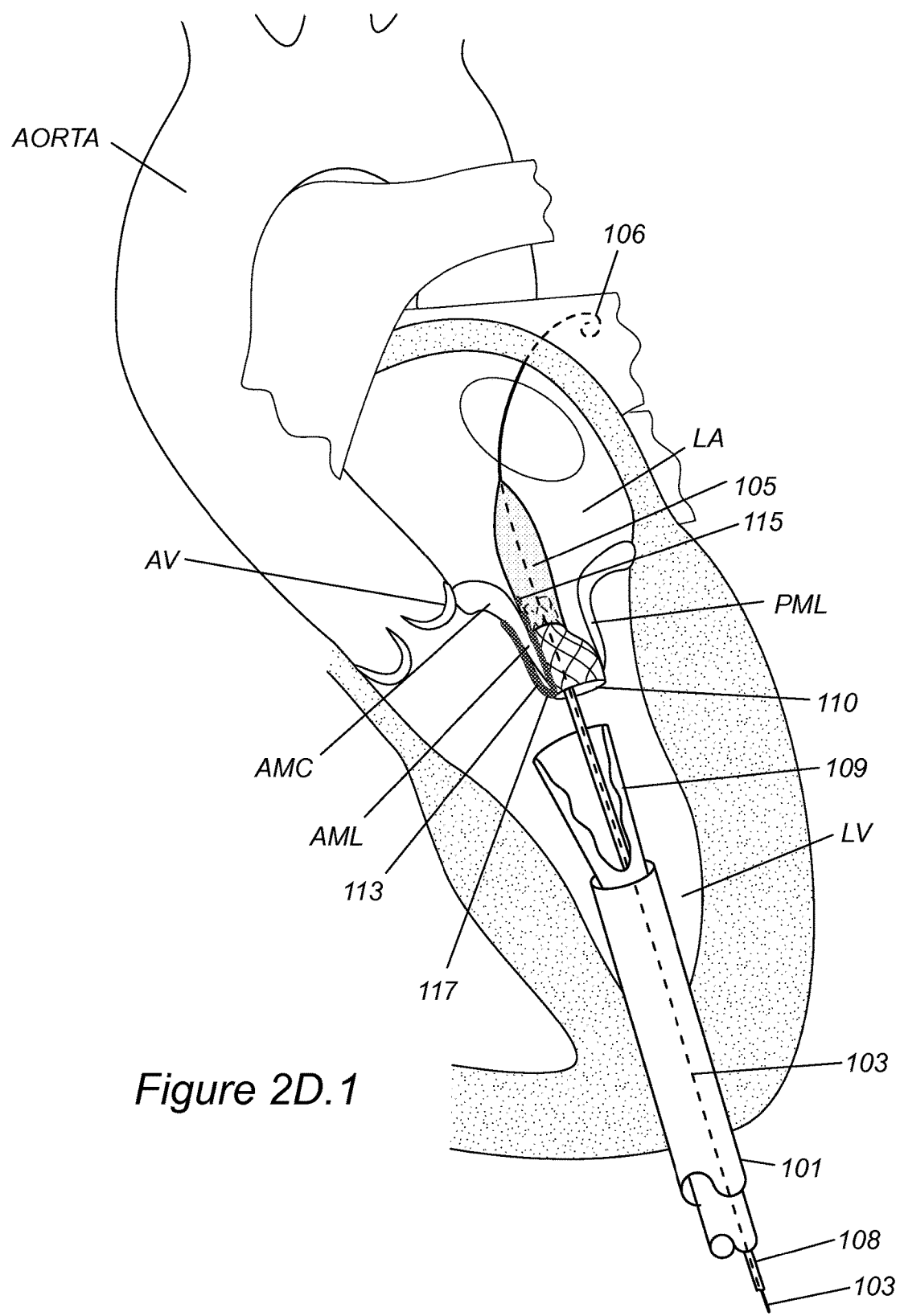
Figure 2D.1

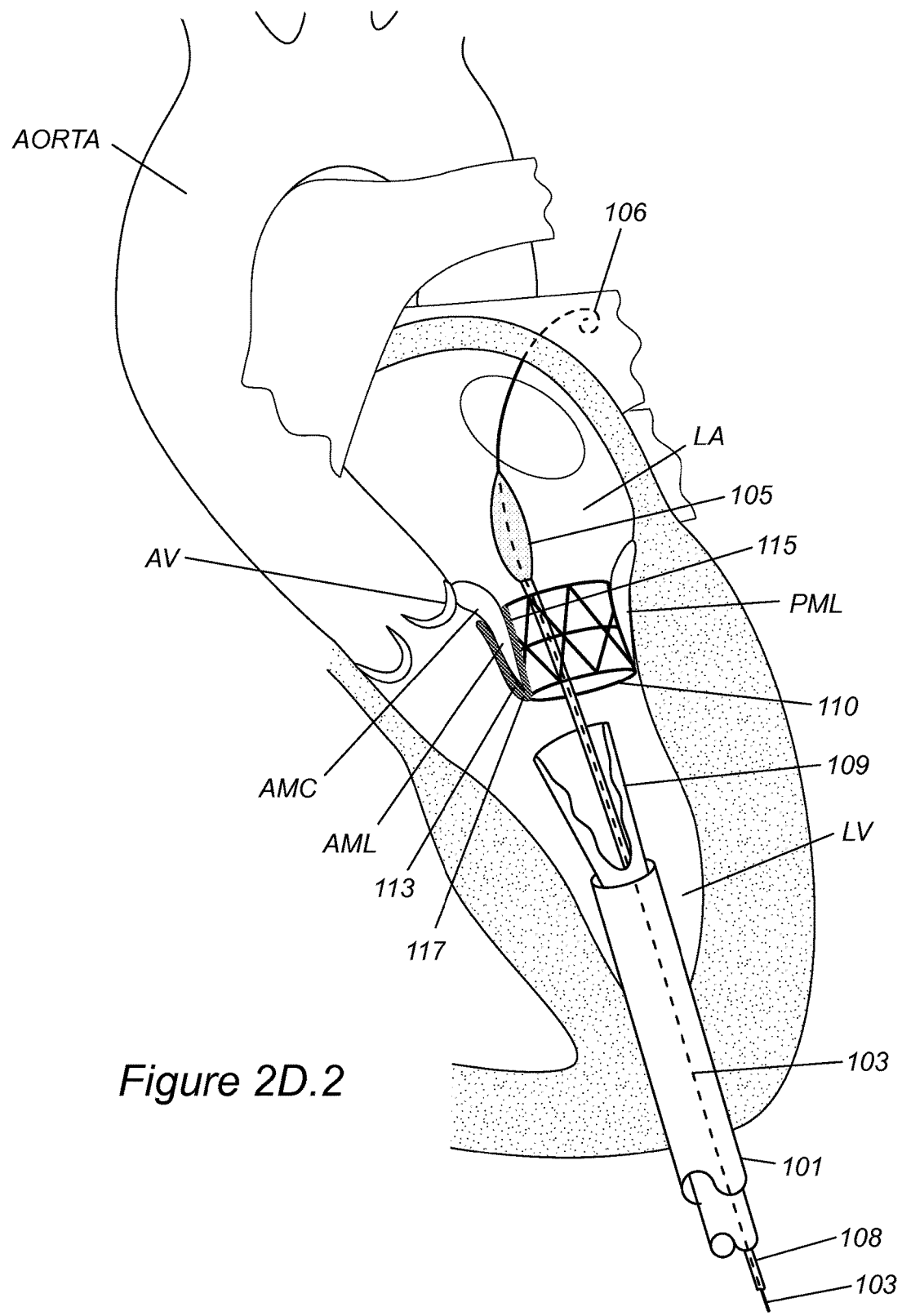
Figure 2D.2

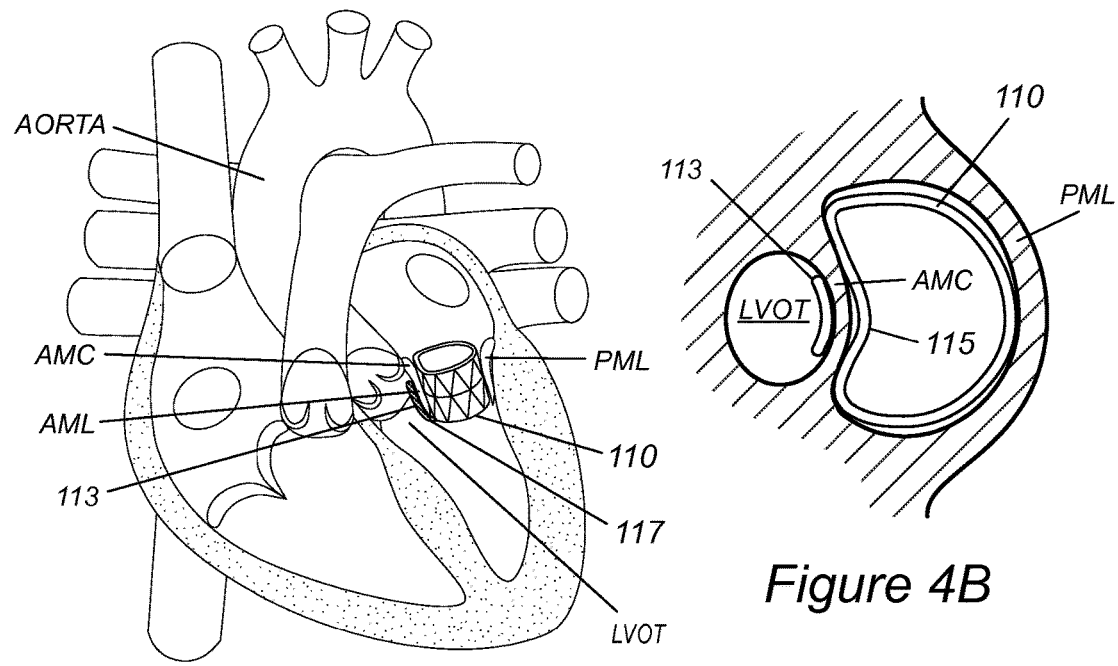
Figure 4A
Figure 4B
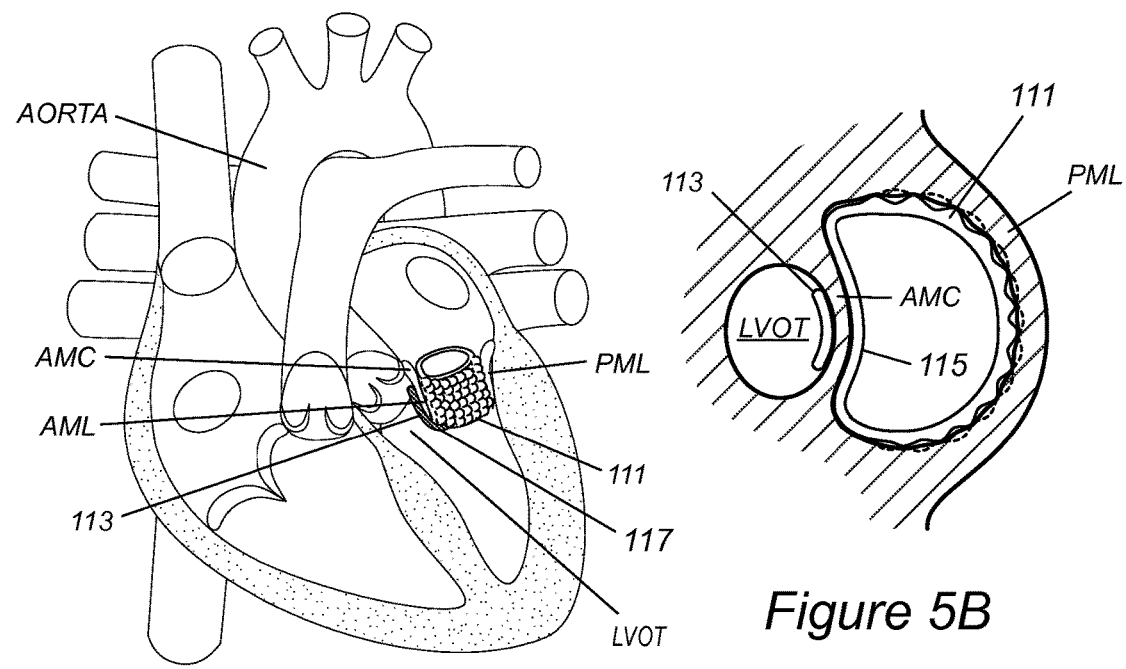
Figure 5A
Figure 5B

ANATOMICALLY-ORIENTATED AND SELF-POSITIONING TRANSCATHETER MITRAL VALVE

CROSS-REFERENCE TO RELATED APPLICATIONS

This application is a National Phase of International Application No. PCT/US2014/060526 filed Oct. 14, 2014, currently pending, which designated the U.S. and that International Application was published under PCT Article 21(2) in English, which also includes a claim of priority under 35 U.S.C. § 119(e) to U.S. provisional patent application No. 61/891,003 filed Oct. 15, 2013, the entirety of which is hereby incorporated by reference.

FIELD OF INVENTION

The present invention is directed to devices, systems and methods for replacing the diseased mitral valve in a subject in need thereof.

BACKGROUND OF THE INVENTION

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The presently available prosthesis for transcatheter mitral valve replacement (TMVR) are not designed to accommodate the unique anatomy of the mitral valve. Therefore, the outcomes of TMVR frequently are not favorable. For instance, incidents of paravalvular regurgitation are higher after deployment of mitral valve prosthesis than for aortic valve prosthesis. Additionally, ventricular outflow tract obstruction has been described after mitral valve repair, despite advances in mitral valve repair. Therefore, there exists a need in the art for an improved mitral valve that lowers the incidence of regurgitation, ventricular outflow tract obstruction, and other common issues that occur after a mitral valve prosthesis is implanted.

SUMMARY OF THE INVENTION

The following embodiments and aspects thereof are described and illustrated in conjunction with systems, compositions and methods which are meant to be exemplary and illustrative, not limiting in scope.

Described herein is a mitral valve and systems and methods for implanting the same. The mitral valve device is designed to easily orient to and conform to the mitral orifice natural morphology. This mitral valve system may be implanted using a system of 2 guide wires that facilitate orientation of the flat portion of the stent properly with the flat portion of the mitral valve that is adjacent to the aortic valve. Additionally, the disclosed valve may have multiple mounds distributed across the outer surface of the valve/stent complex so as to prevent or reduce paravalvular leak after implantation.

The natural morphology of the mitral valve opening is D-shaped, with the flat edge of the "D" along the side that borders the aortic valve. Accordingly, the flow dynamics of a patient's heart are optimized when the orifice of the mitral valve is D shaped. Additionally, the shape of the mitral opening affects the flow of the entering the adjacent aortic valve and other structures in proximity to the mitral valve. However, typical mitral valve prosthesis are circular shaped and/or have flat surfaces that require rotational positioning, and therefore do not automatically conform to the natural geometry of the mitral valve opening. This departure from the nature shape and/or lack of automatic conformity to the mitral valve opening may cause decreased optimization of flow through the mitral valve, aortic valve, and other cardiac structures. Additionally, the circular shape and/or mal-alignment of flat surfaces may have contributed to paravalvular regurgitation, and compression of the ventricular outflow tract due to the fact that the wall adjacent the aortic valve is flat, and therefore a circular valve protrudes into the cardiac tissue that separates mitral valve from the aortic valve.

Thus, the inventors have discovered that there is a need in the art for a prosthetic mitral valve that accommodates the unique shape of the mitral valve opening and further conforms to the natural shape and contours of the mitral valve orifice. Accordingly, disclosed is a valve that is carried or framed by a D-shaped stent, rather than circular. Additionally, in some embodiments, the valve includes multiple mounds or other surface topography to conform to each unique individual valve opening morphology and create a better sealed valve. Additionally, implanting of a D-shaped valve (rather than circular) requires the valve to be properly oriented with the flat edge of the "D" to be aligned and resting on the relatively flat portion of the mitral valve that is adjacent to the aortic valve. Prior methods for implanting non-circular valves have required rotational positioning that may be difficult to optimize, requiring advanced imaging and manipulation. Accordingly, the inventors have developed systems and methods for implanting the D-shaped valve in the correct orientation using two guide wires and catheters. In some embodiments, one of the guide wires is advanced down the aortic valve, and another is advanced down the mitral valve. In some embodiments, one arm of the prosthetic valve may be loaded onto a first catheter traveling on the first guide wire, and the second arm of the prosthetic valve may be loaded onto a second catheter that travels along the second guide wire. Thereafter, the prosthetic valve may be guided in the proper orientation by both guide wires as disclosed in further detail herein.

This prosthetic mitral valve is described further herein in some embodiments as a transcatheter mitral valve with two features, namely, a D-shaped stent that carries a mitral valve having 1, 2 or 3 leaflets. Additionally, the mitral valve is fastened in place in the heart with a U-shaped anchor connected and/or integrated with the D-shaped stent which hooks the mitral valve to the aortic mitral continuity (the fibrous continuity between the aortic valve and the anterior leaflet of the mitral valve) and the anterior mitral leaflet. Additionally, the disclosed mitral valve may have multiple mounds distributed across the outer surface of the valve/stent complex so as to prevent or reduce paravalvular leak after implant. The mounds may be coated with various agents such as antibodies, fibrinogen, etc. that increase the probability of a complete seal with the avoidance of paraprosthetic regurgitation.

Also provided is a system for transcatheter mitral valve replacement. The system includes (i) the device described herein, (ii) a cylindrical sheath, (iii) a first guide wire that is configured to be advanced through the cylindrical sheath and through the aortic valve into the aorta, (iv) a second guide wire that is configured to be advanced through the cylindrical sheath and through the mitral valve and the left atrium into the right upper pulmonary vein, (v) a first catheter that includes a hollow proximal end, a conical closed distal end and an elongated central shaft with a hollow central lumen configured to advance over the first guide wire, (vi) a second catheter that includes a hollow proximal end, a conical closed distal end and an elongated central shaft with a hollow central lumen configured to advance over the second guide wire, (vii) a third catheter that includes proximal end, a distal end, an elongated hollow body wherein the third catheter makes contact with the first and second catheters and the first, second and third catheters are designed to be advanced as one in vivo.

In various embodiments, (1) the valve prosthesis is mounted on the first and second catheters ex vivo, such that the left-arm of the U-shaped anchor is loaded within the first catheter and the right arm of the anchor with the adjoining D-shaped valve is loaded within the second catheter; (2) third catheter forms a main body which makes contact with the proximal ends of the first and second catheters allowing the whole system to be advanced as a single unit through the cylindrical sheath; (3) the cylindrical sheath is configured to be advanced over a guide wire into the left atrium; (4) the first and second guide wires are advanced and retracted independently of each other; (5) the first and second catheters have a proximal aspect that is expandable and collapsible; (6) the proximal aspect of the first catheter forms a carina with the proximal aspect of the second catheter via the U-shaped anchor; and (7) the first and second catheter may be advanced and retracted independently of each other after delivery of the anchor and the valve.

In an additional embodiment an elliptical ring is attached to the left ventricular outflow tract (LVOT) arm of the U-shaped anchor and this ring extends upwards to just below the native valve. This is intended as an anchor for a conventional transcatheter aortic valve replacement (TAVR) device in the presence of co-existing aortic regurgitant disease without significant aortic stenosis. For instance the elliptical ring provides a structure that an aortic valve may fit inside and hook onto with, in some embodiments, hooks around the outside rim of the aortic valve prosthesis. Without such a provision, in this clinical scenario conventional TAVR devices are unstable, as an aortic prosthesis otherwise generally does not have sufficient native cardiac tissue to aid in anchoring or installation.

Accordingly, installation of the disclosed mitral prosthesis provides a unique opportunity to simultaneously implant a support structure or anchor for a prosthetic replacement for the adjacent aortic valve. This allows both artificial valves to anchor to the flap between the aortic valve and the mitral valve, which provides a conveniently thin tissue wall that can be anchored to with a U-shaped, or other shaped anchor that saddles and pinches the tissue.

The elliptical ring may be constructed from the same material as the D-shaped stent as disclosed herein or other suitable materials. In some embodiments, it will only be a relatively thin ring. In other embodiments, the elliptical ring will extend down to just above the aortic valve. For instance, it may extend down to a 1, 2, 3, 4, or 5 mm above the aortic valve. In some embodiments, the ring will have a support structure for a prosthetic aortic valve that is a ring, or other structure to hook onto that is closest to the aortic valve. This may include complementary structures to hook onto, including a ring, or other suitable structures.

BRIEF DESCRIPTION OF FIGURES

Exemplary embodiments are illustrated in the referenced figures. It is intended that the embodiments and figures disclosed herein are to be considered illustrative rather than restrictive.

FIG. 4 depicts, in accordance with various embodiments of the present invention, (A) a schematic of the heart with the valve and the anchor in place; (B) a cross section showing the valve, anchor, LVOT and the AMC.

FIG. 5 depicts, in accordance with various embodiments of the present invention, (A) a heart valve with mounds; (B) a cross section showing the valve, anchor, LVOT and the AMC with the mounds on the rounded portion of the valve.

DETAILED DESCRIPTION OF THE INVENTION

Figure 1:
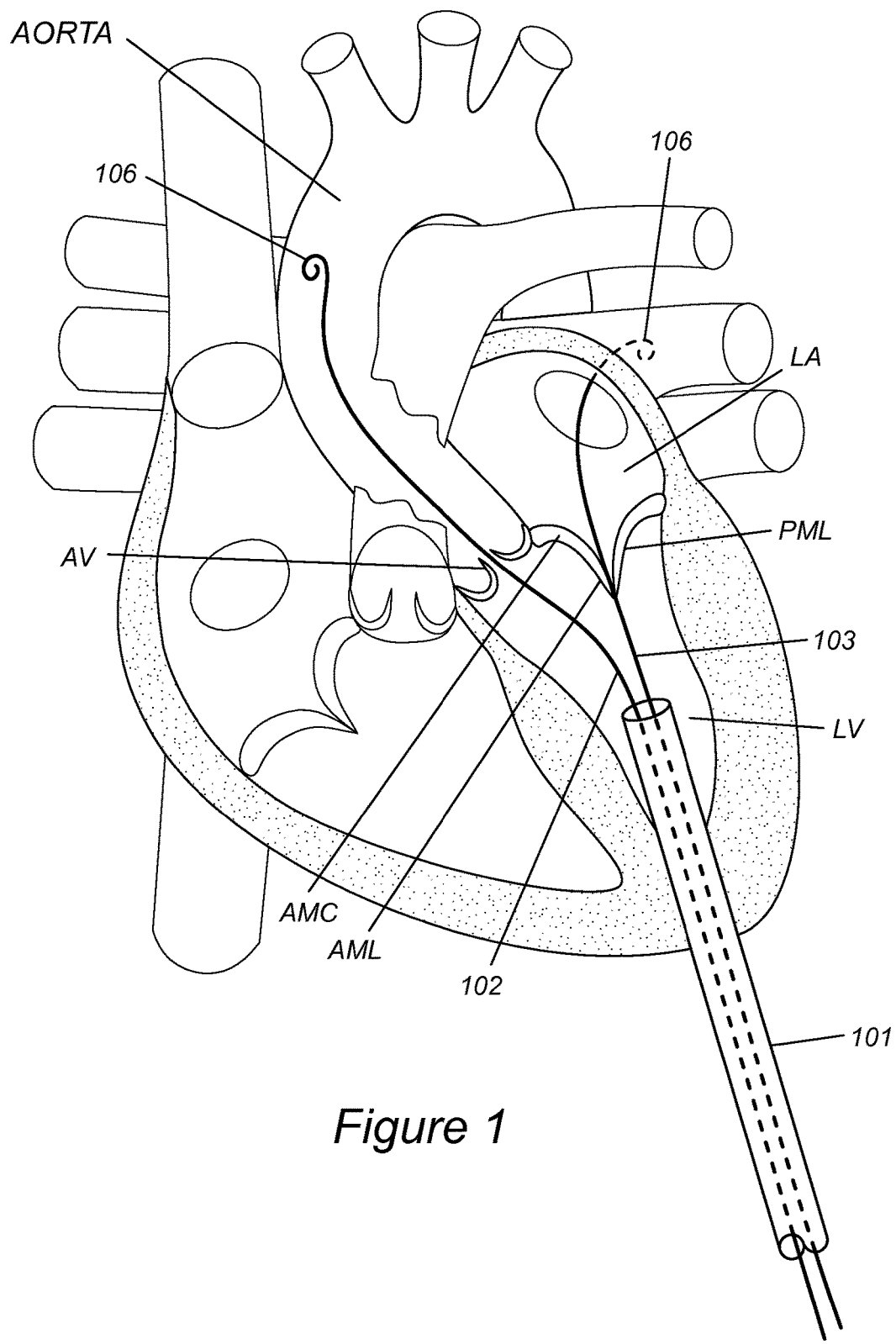
FIG. 1 depicts, in accordance with various embodiments of the present invention, a schematic of the heart with the cylindrical shaft and the first and second guide wires.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Mammal" as used herein refers to any member of the class Mammalia, including, without limitation, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject. The term does not denote a particular age or sex. Thus, adult and newborn subjects, as well as fetuses, whether male or female, are intended to be included within the scope of this term. In certain embodiments, the devices, systems and methods described herein are configured for humans. One of skill in the art would readily appreciate that the devices and methods described herein could be customized for use in almost any animal in which a heart valve may be replaced.

Described herein is a mitral valve and systems and methods for implanting the same. The mitral valve device is designed to easily orient to and conform to the mitral orifice natural morphology. This mitral valve system may be implanted using a system of 2 guide wires that facilitate orientation of the flat portion of the stent properly with the flat portion of the mitral valve that is adjacent to the aortic valve. Additionally, the disclosed valve may have multiple mounds distributed across the outer surface of the valve/stent complex so as to prevent or reduce paravalvular leak after implantation.

As illustrated in FIGS. 4B and 5B, the mitral orifice has a D-shaped, or roughly D-shaped non-circular morphology. It is preferable that a mitral prosthesis be designed to conform to this D-shape to minimize interference with the left ventricular out flow (LVOT) as might result from a circular mitral prosthesis. For instance, as illustrated in FIGS. 4B and 5B, the mitral prosthesis may have a flat portion on one side, and a circular or rounded profile or cross section for the remaining portion of the valve. The stent system that supports the prosthetic valve may accordingly be designed in the D-shape. In some embodiments, the flat portion may be slightly curved to conform to the mitral valve orifice morphology. In other embodiments, slight variations on the D-shape the better conform to the mitral orifice could be developed, to better conform to the mitral valve.

One issue that results from implementing a D-shaped valve is that the D-shaped device must be in the correct orientation upon implantation. However, the rotational positioning during implantation in this setting remains technically challenging. Therefore, there is a need for a device that can be properly orientated during implantation without increasing procedural complexity. Described herein is such a mitral valve, a system for mitral valve replacement and methods for replacing a diseased mitral valve with the mitral valve described herein.

Figure 3:
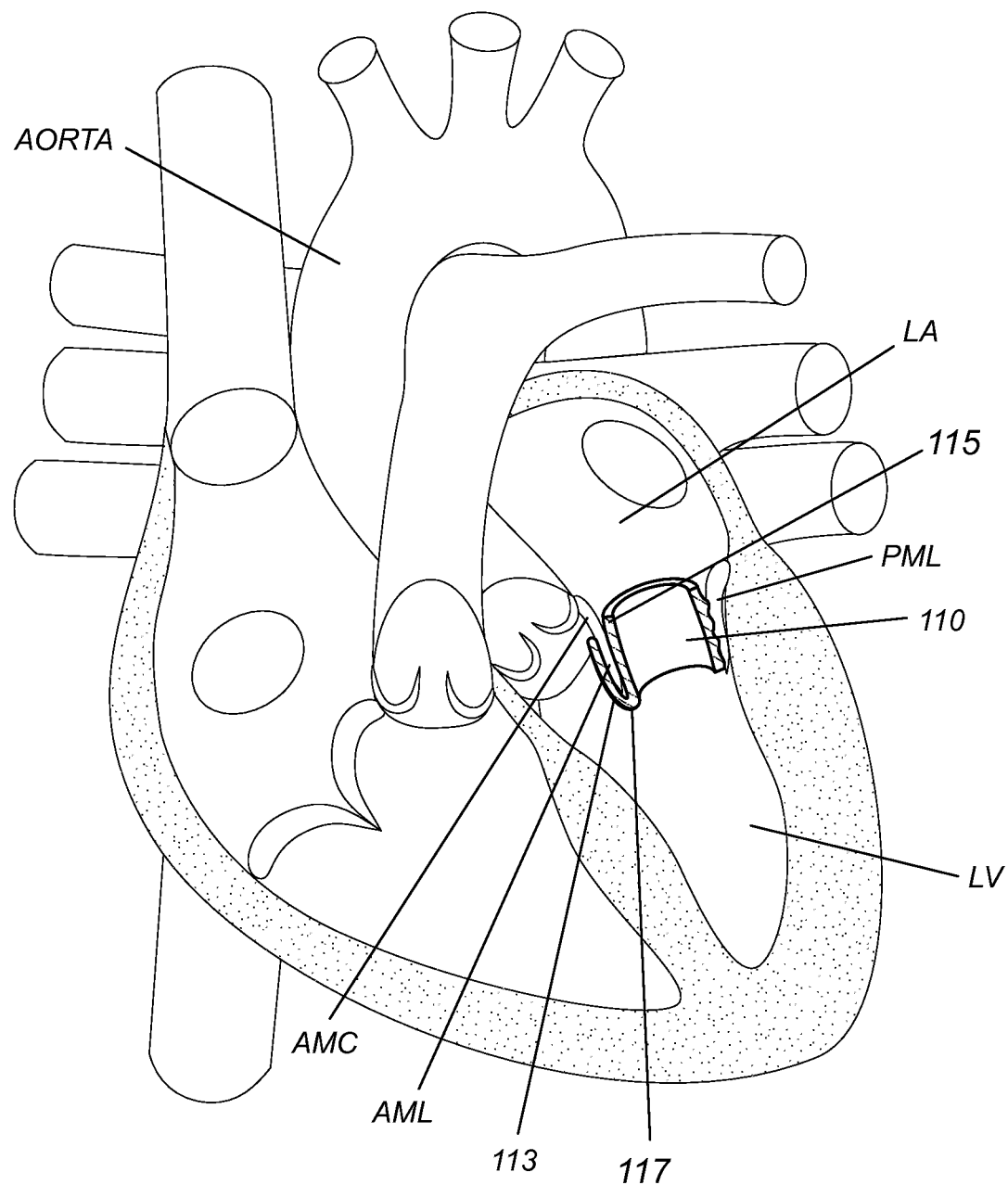
FIG. 3 depicts, in accordance with various embodiments of the present invention, a schematic of the heart with a cross-section of the replaced mitral valve and a U-shaped anchor anchoring the valve stent frame to the anterior and posterior aspects of the aortic mitral continuity and the anterior mitral leaflet.

Provided herein is a device that includes a mitral valve having one, two or three leaflets, a D-shaped stent frame containing the mitral valve and an anchor. The anchor includes a right arm and a left arm so as to anchor the stent frame to the aortic mitral continuity and the anterior mitral leaflet. The right and left arms of the anchor are connected as in a "U" or "V" or similar shape. In some embodiments, and as illustrated in FIG. 3, the right arm of the anchor is continuous with D-shaped stent frame. In some embodiments, the right arm of the anchor is connected or continuous with the flat portion the D-shaped stent frame. In some embodiments the right arm of the anchor is connected to the D-shaped stent frame but has a low profile, or is a rib on the inside surface of the stent while not interfering with the valve flow.

In some embodiments, the outer surface of the mitral valve is smooth (FIGS. 4A and 4B). In some embodiments, the outer surface of the valve has mounds 111 so as to prevent paravalvular leaks (FIGS. 5A and 5B). As illustrated in FIGS. 5A & 5B, the mounds may be round bumps or spherical structures that cover the outside surface of the valve that contacts the patient's heart tissue. In other embodiments, the surface topology of the mitral valve 110 may have other suitable shapes to provide increased sealing between the valve surface and the mitral valve orifice of the heart. In some embodiments, the mounds 111 will only be on the curved portion of the valve, and not on the straight or straighter portion of the "D" shape. In various embodiments, the outer surface of the valve 110, whether smooth or with mounds 111 is coated with therapeutic agents. In various embodiments, the therapeutic agents include but are not limited to pro-coagulant agents or materials such fibrinogen or collagen, antibodies or chemoattractants that may recruit cells, such as CD34 or interleukins.

FIGS. 1 and 2A-2D described the system for mitral valve replacement. The system includes the device 110 described herein, a cylindrical sheath 101, a first guide wire 102 with a spiral or curved end 106, a second guide wire 103 with a spiral end 106, a first catheter 104 with a shaft 107, a second catheter 105 with a shaft 108, and a third catheter 109.

In some embodiments, the device 110 of the system includes a mitral valve having one, two or three leaflets, a D-shaped stent frame containing the mitral valve and an anchor 117. In some embodiments, the anchor 117 may be U-shaped or V-shaped, or other suitable shapes to conform to or cradle the tissue between the aortic valve and the mitral valve (the aortic mitral continuity). In some embodiments, other mitral valve types may be included in the device 110, including a graphite disc valve, bi-leaflet valves which two semicircular leaflets, or other replacement mitral valves. The anchor 117 includes a right arm 115 and a left arm 113 so as to anchor the stent frame to the aortic mitral continuity and the anterior mitral leaflet. The right 115 and left arms 113 of the anchor 117 are connected and in some embodiments, may form a shape similar to a "U" or a "V". In some embodiments, the right 115 and left 113 arms may have wavy or jagged edges to better anchor the device 110 to the cardiac tissue. In other embodiments, either the right 115 or left 113 arms or both may be wavy or undulate, spiral or have other geometries for holding the device 110 in place in the heart.

In some embodiments, the right arm 115 of the anchor 117 may be continuous with D-shaped stent frame. In this embodiment, the right arm 115 will be constructed so that it is a portion or woven into the stent frame, but may retain some rigid characteristics or be a separate support or rigid member within the stent frame in order to fasten the device to the heart aortic mitral continuity. In some embodiments, the right arm 115 will only be comprised of the stent frame, and will have no separate rigid components included therein.

As illustrated in FIG. 1, the cylindrical sheath 101 includes a proximal end, a distal end and an elongated body. The cylindrical sheath 101 is configured to be advanced transapically into the left ventricle (LV). The first guide wire 102 has a proximal end and a spiral distal end 106. The first guide wire 102 is configured to be advanced through the cylindrical sheath 101, through the aortic valve (AV) and into the aorta. The second guide wire 103 includes a proximal end and a spiral or other blunt formation to form a distal end 106. The second guide wire 103 is configured to be advanced through the cylindrical sheath 101, the mitral valve, and the left atrium (LA) into the right upper or other pulmonary vein or advanced as far as possible into the LA. In some embodiments, it will only be advanced halfway into the LA or other portion of the LA.

As illustrated in FIGS. 2A-2D, the first catheter 104 includes a hollow proximal end, a conical closed distal end, and an elongated central shaft 107 with a hollow central lumen configured to advance over the first guide wire 102. The second catheter 105 includes a hollow proximal end, a conical closed distal end and an elongated central shaft 108 with a hollow central lumen configured to advance over the second guide wire 103. The third catheter 109 includes a proximal end, a distal end, an elongated hollow body wherein the third catheter 109 makes contact with the first catheter 104 and second catheter 105 and the first, second and third catheters are configured to be advanced as one in vivo.

Figure 2A:
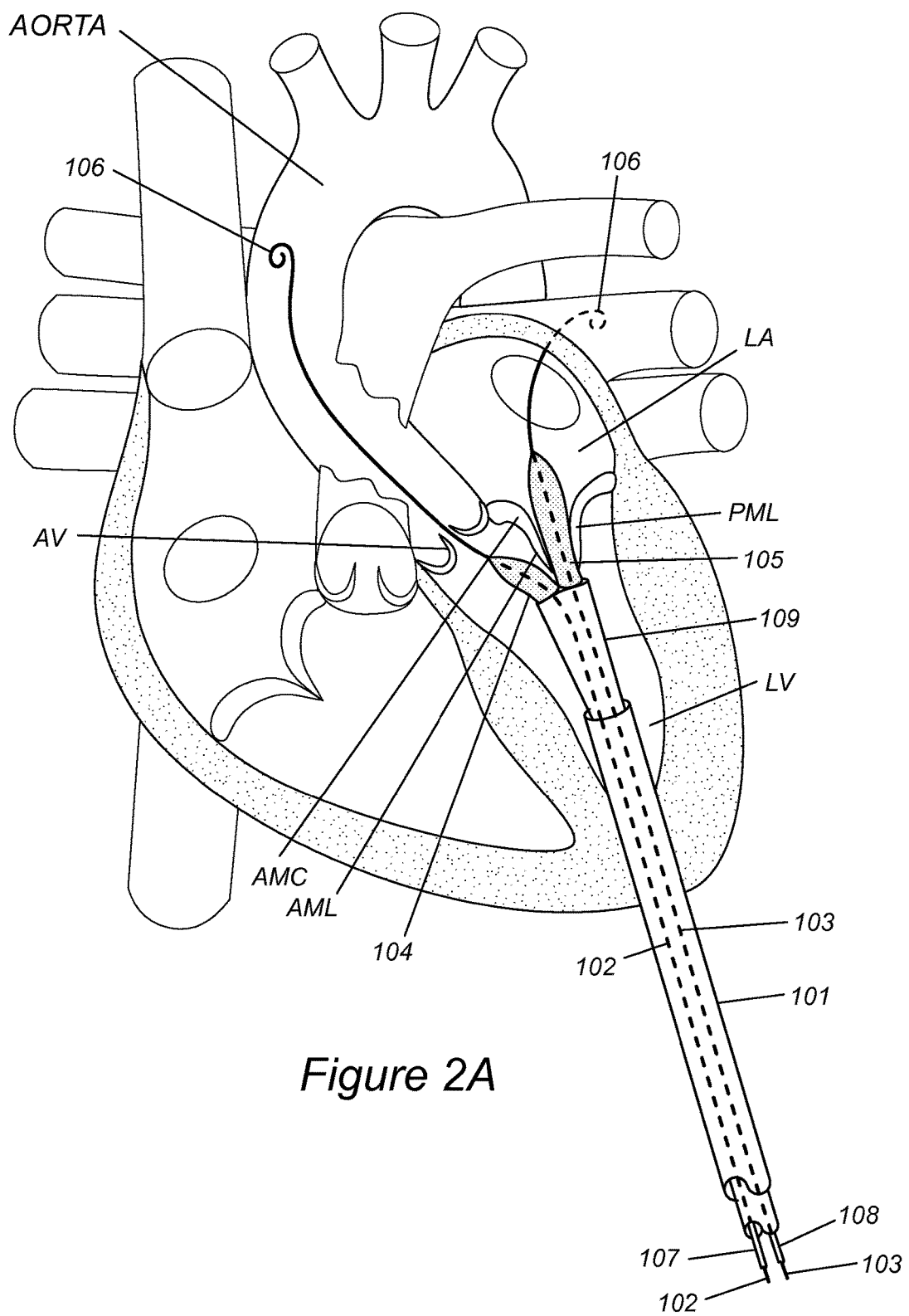
FIG. 2 depicts, in accordance with various embodiments of the present invention, (A) a schematic of the heart with the cylindrical shaft, guide wires, an expanded view of the first, second and third catheters and the shafts within the first and second catheters; (B) a schematic of the heart with a partial cut-away of the third catheter, showing the replacement mitral valve comprising the D-shaped valve and a U-shaped anchor; (C.1) a schematic of the heart with the first catheter fully advanced and the U-shaped anchor in position so as to anchor the valve stent frame to the anterior and posterior aspects of the aortic mitral continuity/anterior mitral leaflet and the second catheter in position and ready to deploy the valve stent comprising the mitral valve; and (C.2) subsequently after the first catheter is removed (D.1) a schematic of the heart with the valve partially deployed as the second catheter is collapsed and (D.2) subsequently, fully deployed as the second catheter is further collapsed.
Figure 2B:
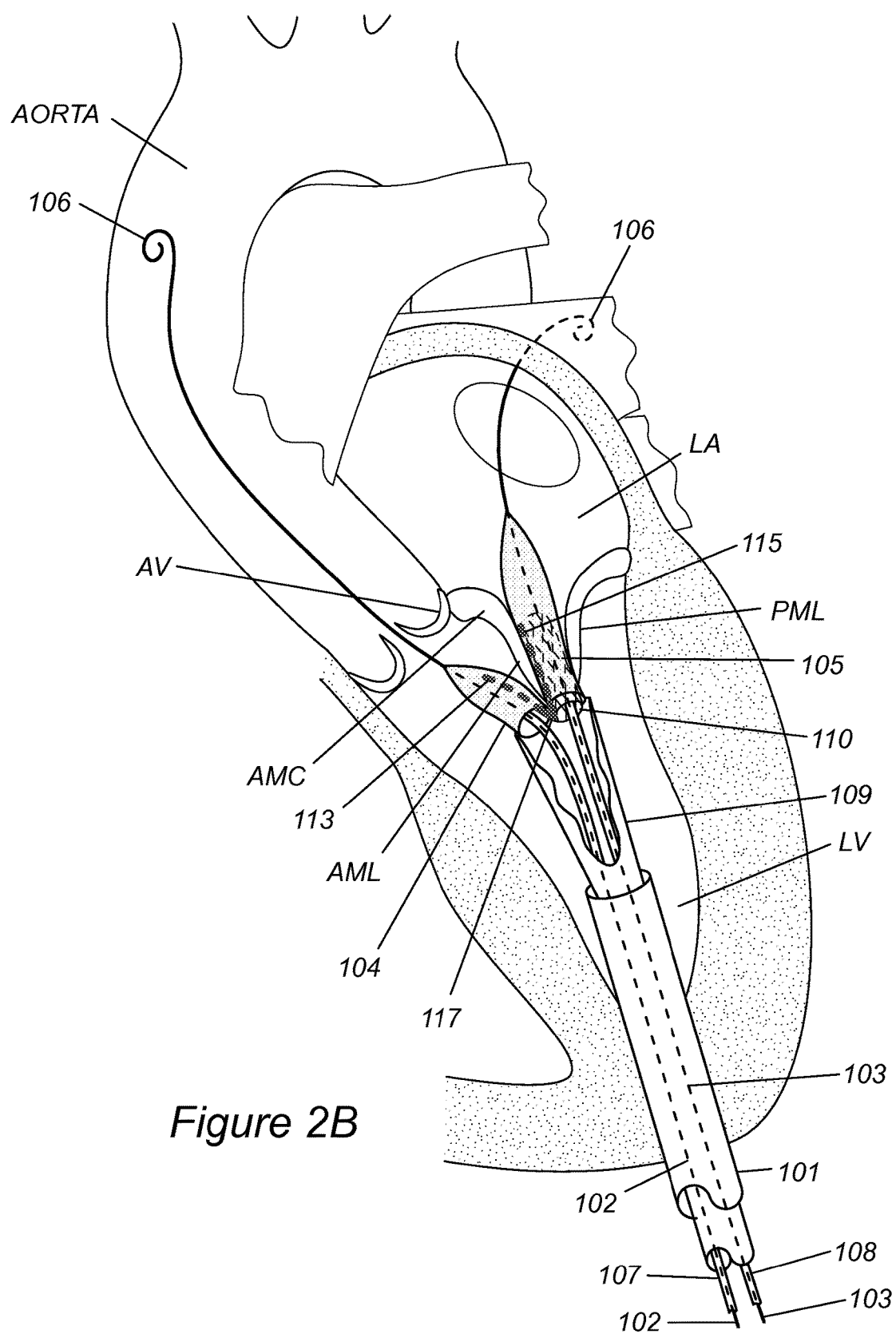

In some embodiments of the system, and as illustrated in FIG. 2B, the valve prosthesis 110 is mounted on the first catheter 104 and second catheter 105 ex vivo, such that the left-arm 113 of the anchor 117 of the valve 110 is loaded within the first catheter 104 and the right arm 115 of the anchor 117 with the adjoining D-shaped valve is loaded within the second catheter 105 (FIG. 2B). In this embodiment, the anchor's 117 apex may saddle the rim of the proximal ends of the first catheter 104 and the second catheter 106 as illustrated in FIG. 2B. In some embodiments, the third catheter 109 forms a main body which makes contact with the proximal ends of the first 104 and second 105 catheters allowing the whole system to be advanced as a single unit through the cylindrical sheath 101 (FIGS. 2A and 2B). In some embodiments, the first catheter 104 and second catheter 105 will be contained partially within the third catheter 109. In some embodiments, the cylindrical sheath 101 is configured to be advanced over the first guide wire 102 and the second guide wire 103 into the left ventricle. In some embodiments, the sheath 101 contains the third catheter 109 within the sheath. In some embodiments, the first guide wire 102 and the second guide wire 103 are advanced and retracted independently of each other. In some embodiments, the first catheter 104 and the second catheter 105 have a proximal aspect that is expandable and collapsible (FIGS. 2B and 2C). For instance, FIG. 2C illustrates the first catheter 104 with the proximal aspect closed and retracted, while the proximal aspect of the second catheter 105 is open. As described herein, the proximal aspect of the first 104 and second 105 catheters may be comprised of nitinol or other shape memory material in order to expand and contract. Additionally, the proximal aspects may include other mechanisms for opening and retracting the proximal aspect. Particularly, once the valve complex 110 is delivered and implanted, the proximal aspects of the first 104 and second 105 catheters may be retracted prior to withdrawal of the catheters to avoid damage to heart tissue or displaying the newly implanted valve. The proximal aspect of the first catheter 104 may form a carina with the proximal aspect of the second catheter via the anchor 117 (FIG. 2B). The first 104 and second 105 catheter may be advanced and retracted independently of each other after delivery of the anchor 117 and the valve. In various embodiments, the subject is human.

Materials suitable for constructing the device 110 including the D-shaped valve and anchor 117 are well known in the art, including nitinol. Many other examples of such materials are described in U.S. Pat. No. 8,498,214 and U.S. Publication No. US2011/0319989, incorporated by reference herein in their entirety.

In various embodiments, the outer diameter of the first catheter may be 8-12 French (Fr). In an embodiment, the outer diameter of the second catheter may be 12-20 Fr in maximal dimension. In various embodiments, the resting or un-flexed distance between the left 113 and right 115 arm of the anchor 117 at various points removed from the apex or connection point between the left 113 and right arm 115 of the anchor 117 is configured so that it provides sufficient tension to hold the first catheter 104 and second catheter 105 together until deployment. Upon deployment, the distance between the left and right arm of the anchor 117 is such that it provides sufficient tension to clip the D-shaped stent comprising the replacement valve to the LVOT and atrial aspects of the anterior mitral leaflet and atrial aspect of the anterior mitral leaflet and the aortic mitral continuity. For instance, in an un-flexed state, the left 113 and right 115 arms would be a first distance apart. When deployed, the flexible material of the anchor 117 would be flexed to expand so that it may clip the heart tissue. The left arm 113 and right arm 115 may then squeeze the heart structure between the left 113 and right 115 arms in order to hold the valve prosthesis 110 in place. In various embodiments, the distance between left 113 and right 115 arms of the anchor 117 may be from 2-5 mm at various distances from the connection point between the left arm 113 and the right arm 115, depending on the thickness of the intervening aortic-mitral continuity/anterior mitral leaflet which the respective arms sandwich. In some embodiments, such the tension may be from a spring, fastener, or coils in the anchor 117 or be an intrinsic property of the material from which it may be constructed, for example nitinol. In other embodiments, the distance between the left arm 113 and right arm 115 may vary with the distance from the connection point between the left 113 and right arms 115.

Also described herein is a method for replacing a diseased mitral valve in a subject in need thereof. The method includes providing (i) a device 110 that includes a mitral valve a D-shaped stent frame containing the mitral valve and an anchor as, (ii) first 104, second 105 and third 109 catheters, (iii) first 102 and second 103 guide wires, (iv) a cylindrical sheath 101, each component for example, as described herein. In various embodiments, the appropriate guide wires, cylindrical sheath and catheters for use with the methods described herein will be apparent to a person of skill in the art, for example, as described in Transapical aortic valve implantation in humans. Ye J, Cheung A, Lichtenstein S V, Carere R G, Thompson C R, Pasupati S, Webb J G. *J Thorac Cardiovasc Surg.* 2006 May; 131(5): 1194-6 and Transapical transcatheter aortic valve implantation in humans: initial clinical experience. Lichtenstein S V, Cheung A, Ye J, Thompson C R, Carere R G, Pasupati S, Webb J G. *Circulation.* 2006 Aug. 8; 114 (6):591-6. Epub 2006 Jul. 31, the contents of each of which are herein incorporated by reference.

The method further comprises, as illustrated in FIG. 1, inserting a cylindrical sheath 101 into the left ventricle of the subject, inserting a first guide wire 102 through the cylindrical sheath 101 into the aorta of the subject and inserting a second guide wire 103 through the cylindrical sheath 101 and into the right upper pulmonary vein through the left atrium of the subject. As illustrated in FIG. 2A, the first 104 and second 105 catheters, surrounded (held together) by the third 109 catheter are simultaneously advanced through the cylindrical sheath 101 and into the left ventricle. As illustrated in FIGS. 2B-2C, the first catheter 104 is advanced across the aortic valve over the first guide wire 102 so that the left arm 113 of the anchor 117 contacts the LVOT aspect of the anterior mitral leaflet and the aortic mitral continuity below the aortic valve, deploying the anchor 117 and retracting the first catheter 104. The second catheter 105 is advanced such that the right arm 115 of the anchor 117 contacts the atrial aspect of the anterior mitral leaflet and the aortic mitral continuity and the D-shaped valve is aligned with the subject's mitral valve. As illustrated in FIGS. 2D.1 and 2D.2, the valve 110 is deployed and the catheters 104, 105, cylindrical sheath 101 and guide wires 102, 103 are retracted.

As illustrated in FIGS. 2B-2C, in some embodiments, when the first catheter 104 is fully advanced its proximal aspect (which may contain, for example nitinol which facilitates elastic recoil) retracts, making the catheter's proximal aspect adhere to its central shaft and assume a conical morphology. Accordingly, the first catheter 104 may include a mechanism to allow the proximal end to retract or collapse once the device 110 is deployed. In some embodiments, the first catheter's 104 proximal end is held open by virtue of the left arm 113 of the anchor 117 being retained inside the first catheter 113 prior to deployment. Then, once the left arm 113 is deployed and slips out of the first catheter 104, the elastic or shape memory material of the left arm 113 springs back and minimizes the profile. This allows the first catheter 104 to be refracted in atraumatic fashion back across the aortic valve and through the main shaft back into the cylindrical sheath and out of the body. This is because the streamlined profile does not get caught or hung up on any structures or portion of the heart tissue when it is retracted.

As illustrated in FIGS. 2D.1-2D.2, in an embodiment, when the second catheter is fully advanced, and the D-shaped valve is deployed, its proximal aspect (which contains, for example, nitinol, which facilitates elastic recoil) retracts, making the catheter's proximal aspect adhere to its central shaft and assume a conical morphology. Accordingly, the second catheter 105 may include a mechanism to allow the proximal end to retract or collapse once the device 110 is deployed. In some embodiments, the second catheter's 105 proximal end is held open by virtue of the device 110, and right arm 115 of the anchor 117 being retained inside the second catheter 105 prior to deployment. Then, once the left arm 113 is deployed and slips out of the first catheter 104, the elastic or shape memory material of the left arm 113 springs back and minimizes the profile and stream lines it on the proximal end. It is then retracted in atraumatic fashion back across the central lumen of the D-shaped valve and through the main shaft back into the cylindrical sheath and out of the body. This is because the streamlined profile does not get caught or hung up on any structures or portion of the heart tissue when it is retracted.

In various embodiments, the replacement mitral valve is inserted transapically. In an embodiment, the subject is human. In some embodiments, the D-shaped replacement valve is anchored anteriorly with its U-shaped anchor anchored to the LVOT and the atrial aspects of the aortic mitral continuity and the anterior mitral leaflet respectively and makes contact with the posterior mitral leaflet and adjacent aspects of the left atrium and left ventricle posteriorly. In various embodiments, the device includes multiple mounts wherein the mounds of the device in its posterior aspect prevent paravalvular leak at this location. The mounds, in some embodiments, fill in the gaps created by mismatches between the heart wall and the D-shaped replacement valve.

Figure 6A:
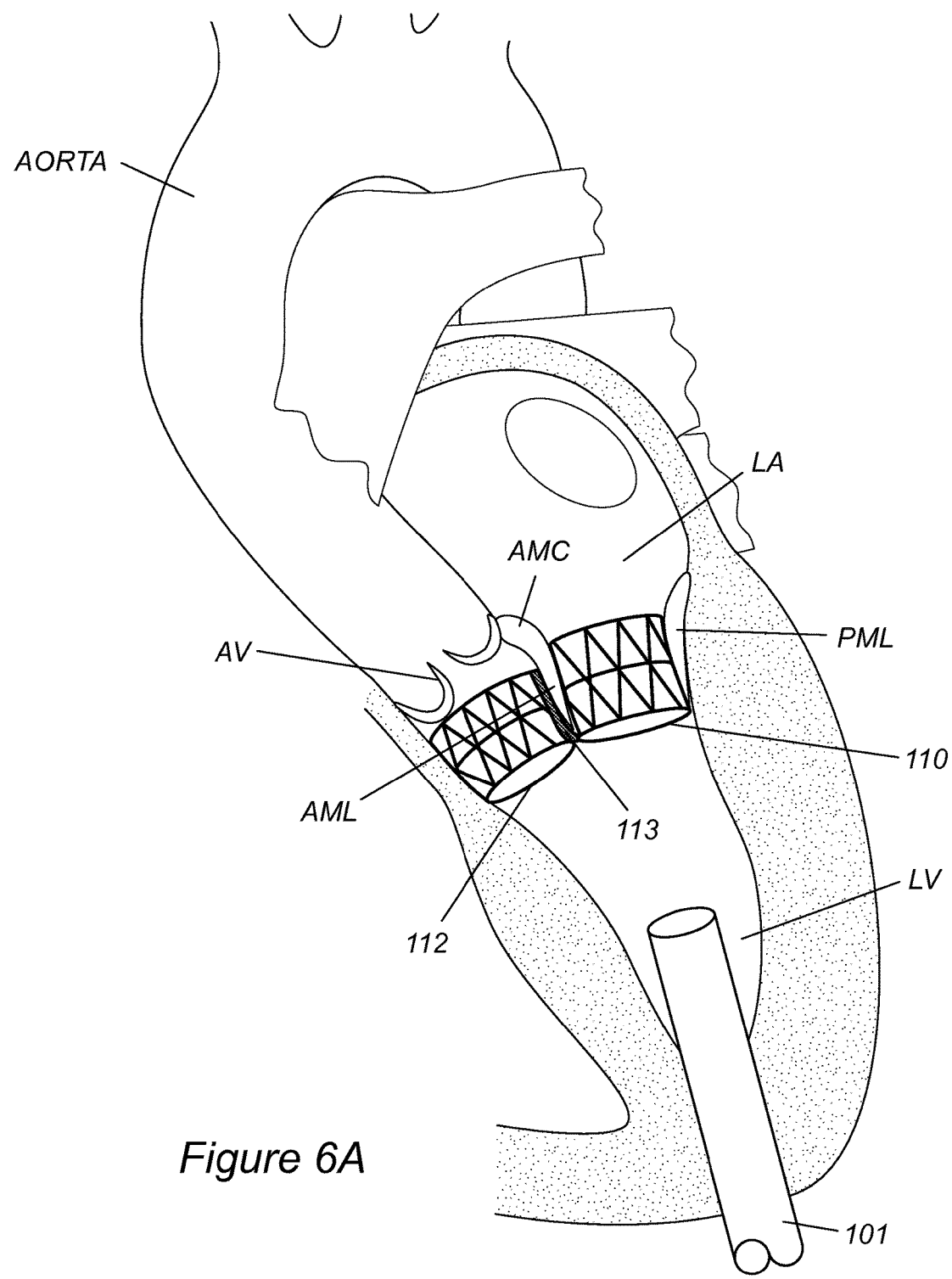
FIG. 6 depicts, in accordance with various embodiments of the present invention, (A) an elliptical ring attached to the LVOT (left) arm of the U-shaped anchor and this ring extends upwards to just below the native aortic valve; and (B) an elliptical ring attached to the LVOT (left) arm of the U-shaped anchor and a broken line depiction of a prosthetic aortic valve attached to the elliptical ring.
Figure 6B:
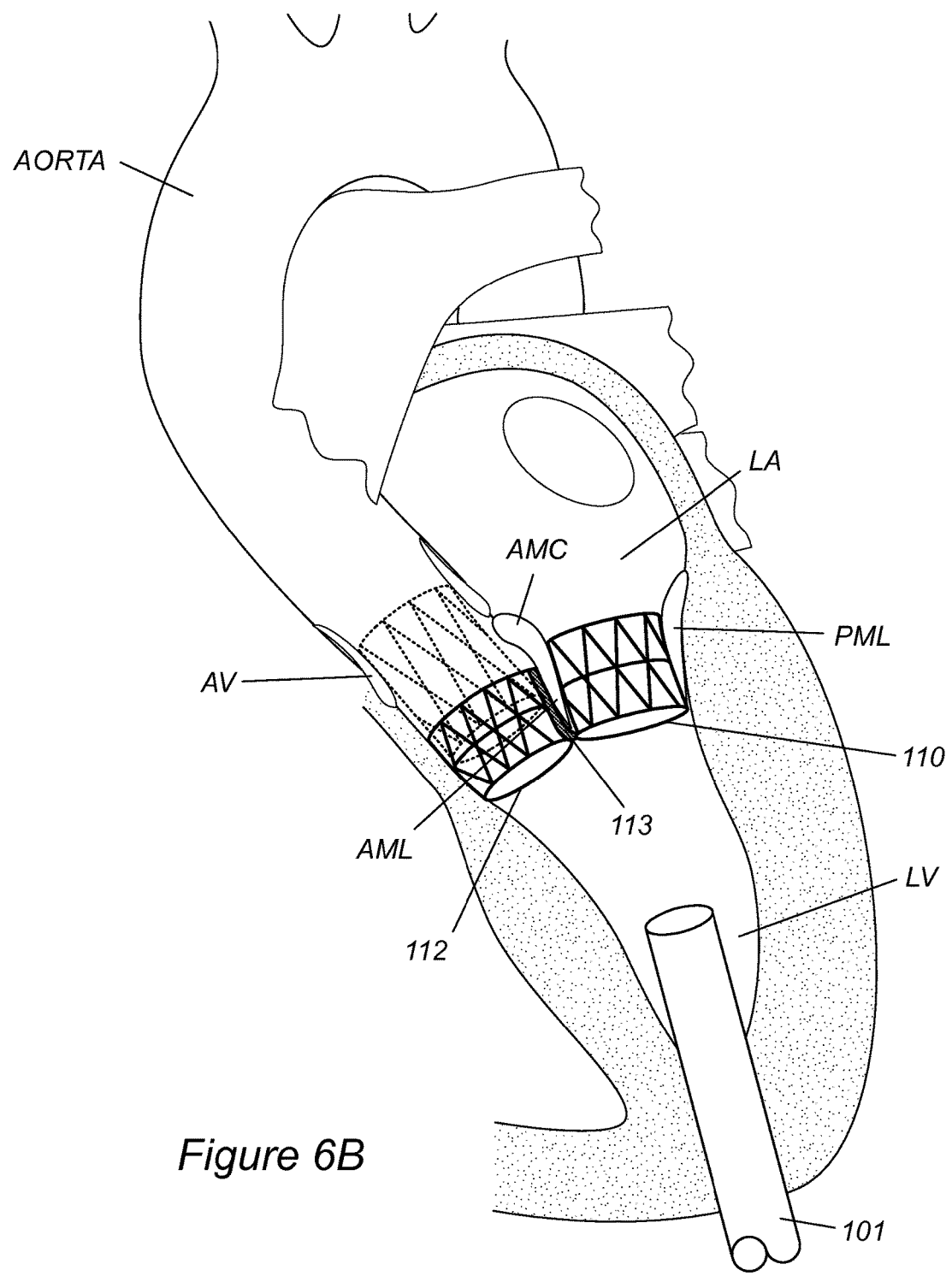

FIG. 6A illustrates an additional embodiment in which an elliptical ring 112 is attached to the left ventricular outflow tract (LVOT) arm 113 of the anchor 117 and this ring 12 extends upwards to just below the native valve. This is intended as an anchor for a conventional transcatheter aortic valve replacement (TAVR) device in the presence of co-existing aortic regurgitant disease without significant aortic stenosis. For instance, the elliptical ring 112 provides a structure that an aortic valve may fit inside and hook onto with, in some embodiments, hooks around the outside rim of the aortic valve prosthesis as illustrated in FIG. 6B. Without such a provision, in this clinical scenario conventional TAVR devices are unstable, as an aortic prosthesis otherwise generally does not have sufficient native cardiac tissue to aid in anchoring or installation.

Accordingly, installation of the disclosed mitral prosthesis provides a unique opportunity to simultaneously implant a support structure or anchor for a prosthetic replacement for the adjacent aortic valve (AV). This allows both artificial valves to anchor to the flap between the aortic valve and the mitral valve, which provides a conveniently thin tissue wall that can be anchored to with a U shaped, or other shaped anchor that saddles and pinches the tissue.

The elliptical ring 112 may be constructed from the same material as the D-shaped stent as disclosed herein or other suitable materials. In some embodiments, it will only be a relatively thin ring. In other embodiments, the elliptical ring 112 will extend down to just above the aortic valve (AV) as illustrated in FIGS. 6A-6B. In some embodiments, the ring 112 will have a support structure for a prosthetic aortic valve that is a ring as illustrated in FIGS. 6A-6B, or other structure to hook onto that is closest to the aortic valve. This may include complementary structures to hook onto, including a ring, or other suitable structures.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Surgical Procedure

After induction of anesthesia, and sterile preparation, an incision is performed at the 5th intercostal space in the mid-clavicular line, cutting the intercostal muscles, and entering the left pleural cavity. Next, the pericardium over the left ventricular apex is opened, and four pledgeted sutures are placed at the site of entry. Next an 18 gauge needle and 0.035" regular J-wire is inserted and advanced through the aortic valve. The needle is withdrawn and a 7 Fr sheath is used to cross the aortic valve over the wire and used to exchange out for a stiffer 0.035" wire (Amplatzer Extra Stiff J-wire or equivalent). The 24 Fr sheath is inserted into the left ventricle over this wire. The subject is heparinized with an activated clotting time (ACT) over 250 sec.

A 0.035" regular J-wire is inserted with a 6 Fr JR4 catheter and advanced through the apical sheath alongside the first wire and from the left ventricle, across the mitral valve and into the right upper pulmonary vein. The JR4 catheter is advanced over the wire to the right upper pulmonary vein (RUPV) and used to exchange out for a stiffer 0.035" wire.

The Transcatheter mitral valve replacement (TMVR) delivery system is advanced through the transapical sheath on both wires such that the longer nose cone is on the RUPV wire. The whole system is advanced such that the carina between the two nose cones in contact with the tip of the anterior mitral leaflet.

The LVOT nose cone is advanced across the aortic valve, deploying the LVOT arm of the anchor. The LVOT nose cone is then withdrawn and removed along with its wire.

The atrial nose cone is then advanced across the mitral valve deploying the atrial aspect of the U-shaped anchor anteriorly and the posterior aspect of the mitral prosthesis posteriorly. The atrial nose cone is then withdrawn and removed. The third central catheter is also removed.

A pigtail is inserted over the wire to the left atrium and a pressure is measured between LA and LV. The pigtail is then pulled back to the LV and a final injection in a right anterior oblique projection is made to observe the residual mitral regurgitation which is also assessed with transesophageal echocardiography at several timepoints.

On withdrawal of the sheath, the transapical access is repaired by ligating the pledgeted sutures, closing the incision in three layers, and leaving a drain in the left chest cavity. Heparin is reversed using protamine to optimize hemostasis.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A system for mitral valve replacement in a subject in need thereof comprising:
   a mitral valve
   a D-shaped stent frame connected to the mitral valve;
   an anchor comprising a right arm and a left arm, wherein the right arm of the anchor is connected to the D-shaped stent frame and the right and the left arm of the anchor are connected;
   a cylindrical sheath, comprising:
      a proximal end, a distal end and an elongated body, wherein the cylindrical sheath is configured to be advanced transapically into the left ventricle;

a first guide wire, comprising a proximal end and a distal end, wherein
  the first guide wire is configured to be advanced through the cylindrical sheath and through the aortic valve into the aorta;
a second guide wire comprising a proximal end and a distal end, wherein the second guide wire is configured to be advanced through the cylindrical sheath, mitral valve and the left atrium into the right upper pulmonary vein, and wherein the second and first guide wires are configured to be advanced and retracted independently of each other;
a first catheter, comprising:
  a hollow proximal end, a conical closed distal end and an elongated central shaft with a hollow central lumen configured to advance over the first guide wire, wherein the hollow proximal end of the first catheter is expandable and collapsible and wherein the first catheter is configured to carry the left arm of the anchor;
a second catheter, comprising:
  a hollow proximal end, a conical closed distal end and an elongated central shaft with a hollow central lumen configured to advance over the second guide wire, wherein the hollow proximal end of the second catheter is expandable and collapsible and wherein the second catheter is configured to carry the right arm of the anchor; and
a third catheter comprising:
  a proximal end, a distal end, an elongated hollow body wherein the third catheter makes contact with the first and second catheters and the first, second and third catheters are designed to be advanced as one in vivo.

2. The system of claim 1, wherein the anchor is U-shaped.

3. The system of claim 1, wherein the first and second catheters are configured so that they may be advanced and retracted independently of each other.

4. The system of claim 1, wherein the mitral valve has mounds that are configured to prevent paravalvular leaks.

5. The system of claim 4, wherein the mounds are coated with therapeutic agents.

6. The system of claim 5, wherein the therapeutic agents comprise one or more of: pro-coagulant agents or, fibrinogen, collagen, antibodies, or chemoattractants that may recruit cells.

7. The system of claim 1, wherein the mitral valve comprises one, two or three leaflets.

8. A method for replacing a diseased mitral valve in a subject in need thereof comprising:
  providing the system of claim 1;
  loading the left and right arms of the anchor into the first and second catheters respectively;
  positioning the third catheter, so that the proximal end of the third catheter surrounds the proximal end of the first and second catheters;
  inserting the cylindrical sheath into the left ventricle of the subject;
  inserting the first guide wire through the cylindrical sheath into the aorta of the subject;
  inserting the second guide wire through the cylindrical sheath and into the right upper pulmonary vein through the left atrium of the subject;
  simultaneously advancing the first, second and third catheters through the cylindrical sheath into the left ventricle;
  advancing the first catheter across the aortic valve over the first guide wire so that the left arm of the anchor contacts the LVOT aspect of the anterior mitral leaflet and the aortic mitral continuity below the aortic valve;
  deploying the anchor and retracting the first catheter;
  advancing the second catheter such that the right arm of the anchor contacts the atrial aspect of the anterior mitral leaflet and the aortic mitral continuity and the D-shaped valve is aligned with the subject's mitral valve;
  deploying the D-shaped valve; retracting the second and third catheter;
  and retracting the guide wires and the cylindrical shaft.

9. The method of claim 8, wherein the subject is a mammal.

10. The method of claim 9, wherein the subject is a human.

11. The method of claim 9, wherein the anchor is U-shaped.

* * * * *